United States Patent [19]

Convent

[11] 4,276,079
[45] Jun. 30, 1981

[54] SYNERGISTIC HERBICIDAL COMPOSITION COMPRISING N-(BUTOXYMETHYL)-6'-TERT-BUTYL-2-CHLORO-O-ACETOTOLUIDIDE AND TRIALLATE

[75] Inventor: Bernard Convent, Leernes, Belgium

[73] Assignee: Monsanto Company, St. Louis, Mo.

[21] Appl. No.: 605,568

[22] Filed: Aug. 18, 1975

[51] Int. Cl.² .................... A01N 9/12; A01N 9/20
[52] U.S. Cl. ......................................... 71/100; 71/118
[58] Field of Search ............................. 71/100, 118

[56] References Cited
U.S. PATENT DOCUMENTS

| 3,330,643 | 7/1967 | Harman et al. | 71/100 |
| 3,330,821 | 7/1967 | Harman et al. | 71/100 |
| 3,442,945 | 5/1969 | Olin | 71/118 |
| 3,547,620 | 12/1970 | Olin | 71/118 |

OTHER PUBLICATIONS

Koslov, "Effect of Avadex and triallate, etc.," (1967), CA68, No. 38442u (1968).
Bachthaler et al., "Double treatment of sugar, etc.," (1967), CA67 No. 72695m (1967).

Primary Examiner—Glennon H. Hollrah
Attorney, Agent, or Firm—Richard H. Shear; Donald W. Peterson

[57] ABSTRACT

A synergistic herbicidal composition comprising as the active ingredient a mixture of N-(butoxymethyl)-6'-tert-butyl-2-chloro-o-acetotoluidide and S-(2,3,3-trichloroallyl) N,N-diisopropylthiocarbamate and use of said composition particularly in sugarbeets and in cereal crops, e.g., wheat and barley.

1 Claim, 2 Drawing Figures

SYNERGISTIC HERBICIDAL COMPOSITION COMPRISING N-(BUTOXYMETHYL)-6'-TERT-BUTYL-2-CHLORO-O-ACETOTOLUIDIDE AND TRIALLATE

BACKGROUND OF THE INVENTION

Field of the Invention

The invention herein pertains to the field of herbicides. In particular, the invention pertains to a synergistic herbicidal composition having as the active ingredient a mixture of N-(butoxymethyl)-6'-tert-butyl-2-chloro-o-acetotoluidide and S-(2,3,3-trichloroallyl)N,N-diisopropylthiocarbamate (common name "triallate"). The herbicidal composition herein has particular application in the control of undesired plants associated with sugarbeets and cereal crops, e.g., wheat and barley.

DESCRIPTION OF THE PRIOR ART

It is known in the prior art to use various carbamates or thiolcarbamates as herbicides, either individually or in combination with various other herbicidal compounds. In such carbamate compounds, the nitrogen substituents and ester moieties are commonly phenyl, benzyl, alkyl or alkenyl groups which may be substituted with halogen or alkoxy groups, but other groups may also be used.

The particular thiolcarbamate of interest herein and use as a component of the combination herbicide of the present invention, i.e., S-(2,3,3-trichloroallyl)N,N-diisopropylthiocarbamate ("triallate" hereinafter for brevity), is a known compound having herbicidal use. The preparation of triallate, herbicidal compositions containing same and use thereof are covered in U.S. Pat. Nos. 3,167,571, 3,330,821 and 3,330,643. In addition, triallate is the active ingredient in Monsanto Company's commercial Avadex BW and Far-go herbicides; "Avadex" and "Far-go" are registered trademarks of that company.

A variety of chemical compounds have been admixed with various members of the above-mentioned carbamates in efforts to discover new herbicidal compositions having unique additive, antagonistic or synergistic properties with respect to different weed plants associated with various crop plants. Illustrative of prior art herbicide mixtures containing carbamates and other herbicidal compounds are those containing various aryl alkyl ureas such as fenuron (1,1-dimethyl-3-phenylurea), monuron (1,1-dimethyl-3-p-chlorophenylurea), diuron (1,1-dimethyl-3-(3,4-dichlorophenylurea), neburon [3,-(3,4-dichlorophenyl)-1-n-butyl-1-methylurea)], or similar ureas wherein the nitrogen or phenyl groups are substituted with a methoxy radical (U.S. Pat. No. 3,095,299 and Belgian Pat. No. 819,097). Other carbamate herbicide mixtures contain 1-phenyl-4-amino-5-chloropyridazine (Belgian Pat. No. 810,793); or a 4,4'-bipyridylium quaternary salt (Japanese Pat. No. 7,204,000); or 3,4-dichloropropionanilide (Japanese Pat. No. 7,301,486); or 2,4-D and/or MCPA (British Pat. No. 1,301,613); or pentachlorophenol or a salt thereof (Japanese Pat. No. 7,102,520). Triallate is the thiocarbamate component in the above Belgian Pat. Nos. 810,793 and 819,097 and Japanese Pat. No. 7204000.

It is also known in the prior art to use various 2-halo-2',6'-dialkyl-N-(alkoxyalkyl) acetanilides as herbicides either individually or in combination with other herbicidal compounds. For example, U.S. Pat. No. 3,551,132 discloses the herbicidal use of 2-chloro-2',6'-diethyl-N-(methoxymethyl) acetanilide (common name alachlor) admixed with 3'-(carbamoyloxy) anilides. British Pat. No. 1,176,547 discloses the herbicidal use of a mixture of alachlor and linuron, i.e., 3-(3,4-dichlorophenyl)-1-methoxy-1-methylurea. U.S. Pat. Nos. 3,442,945 and 3,547,620 disclose a broad class of herbicidal 2-halo-2',6'-dialkyl-N-(alkoxyalkyl) acetanilides, expressly including N-(butoxymethyl)-6'-tert-butyl-2-chloro-o-acetotoluidide; this compound has tentatively been designated as "terbuchlor"; (an application by applicant's assignee is pending before the American Standards Institute for registration of this name as the common name for said compound). Hence, the term "terbuchlor" will sometimes be used hereafter in the specification for brevity.

To applicant's knowledge, there has been no recognition or disclosure in the prior art of a herbicidal composition comprising terbuchlor and a thiocarbamate, in particular, triallate, which together impart complementary, supplementary and/or synergistic action with respect, particularly, to undesirable vegetation associated with sugarbeets and cereal crops, such as wheat and barley.

The phenomenon of synergism is well known to those skilled in the art and, in the herbicidal art, relates to herbicidal compositions of mixed components whose total herbicidal effect is unexpectedly greater than the additive effect of the individual components on particular plants or a spectrum of plants. The use of synergistic mixtures for the control of plant growth permits the utilization of a lesser total amount of herbicidal composition and/or lesser quantities of individual components in the composition to obtain the same or improved results than are obtained when a greater amount of herbicidal composition containing only the individual components or additive mixtures thereof. The use of lesser quantities of active ingredients in a herbicidal composition may also increase the margin of crop safety in the use of those active ingredients.

The concepts of synergism and antagonism (i.e., negative, neutralizing or nullifying effect of one component on another component) in herbicidal combinations have been reduced to mathematical formulation and graphical representation by some authors. For example, by the method described by S. R. Colby in "Weeds", Vol. 15, No. 1 (1967) pgs. 20–22, the expected response of a combination of herbicides is obtained by taking the product of the percent-of-control values for the individual herbicides and dividing by $(100)^{n-1}$ where n is the number of herbicides in the combination.

Another method of expressing synergism and antagonism is described by P. M. L. Tammes in "Netherlands Journal of Plant Pathology", 70 (1964), 73–80. By the Tammes method, a graphic representation is given of the effect of mixtures of herbicides. Each of the components is expressed as a coordinate on a graph and a quantitatively defined effect, e.g., a percent plant mortality, e.g., 50%, 85%, etc., is inserted in the graph. These values are obtained by interpolation. The line which connects the points is called an "isobole". With an isobole the effect of different proportions of the individual components can be evaluated. The Tammes isoboles method has proven reliable in evaluating the synergistic effect of the herbicidal composition of this invention.

As used herein the term "active ingredient" denotes a mixture of terbuchlor and triallate having the combined supplementary, complementary and synergistic properties unique to this mixture.

The term "plant" as used herein encompasses dormant seeds, germinant seeds, germinative seeds, emerging seedlings and established vegetation including roots and above-ground portions.

The term "control" as used herein is inclusive of the effects of killing, inhibiting the growth, reproduction or proliferation and removing, destroying or otherwise diminishing the occurrence or activity of plants and is applicable to any of the stated effects or combinations thereof.

SUMMARY OF THE INVENTION

The present invention relates to a synergistic herbicidal composition containing as the active ingredient therein a mixture of terbuchlor and triallate as above defined, and to the herbicidal use of such compositions particularly useful in cereal crops, e.g., wheat and barley, and in sugarbeets, to control undesired plants such as *Galium aparine* and *Chenopodium album*.

DESCRIPTION OF PREFERRED EMBODIMENTS

EXAMPLE

Figure 1:
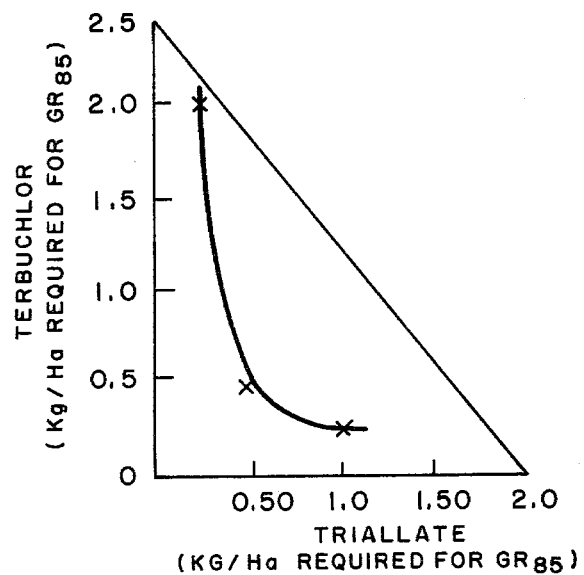

Terbuchlor may be prepared by methods generally known to the art. For example, in Example 4 of each of the above-cited U.S. Pat. Nos. 3,442,945 and 3,547,620, terbuchlor is prepared by reacting 2-tert-butyl-6-methyl-N-methyleneaniline and chloroacetyl chloride with n-butanol according to conditions noted in the example.

Triallate also may be prepared by known methods commonly used to prepare thiocarbamates. See the above-cited U.S. Pat. Nos. 3,167,571, 3,330,821 and 3,330,643. As disclosed, e.g., in U.S. Pat. No. 3,330,821, several methods are available for the preparation of thiocarbamate esters. For example, in one method the halide corresponding to the desired ester is condensed with an alkali metal thiocarbamate The alkali metal thiocarbamates are prepared by the reaction of carbonoxysulfide with amines in the presence of alkali. In another method, a thionocarbamate ester is rearranged to a thiol ester by reaction with an alkyl halide; the rearrangement being accompanied by transesterification. Yet another method for the preparation of thiocarbamates is to condense a carbonyl halide with a mercaptan of mercaptide.

Terbuchlor and triallate were applied as a tank mix and incorporated into a cover layer of a sandy loam soil contained in plastic pots and previously sown with crop and weed seeds at 1 cm depth. Application of the mixed herbicide was made at a volume equivalent of 4000 l/ha with a Devilbiss atomizer No. 152. Initial irrigation of 1 mm was applied by overhead means and subsequent watering requirements by subirrigation. The plants were visually observed approximately three weeks after sowing and the results recorded.

The synergistic response for terbuchlor/triallate herbicidal mixtures is well shown by data in Tables 1 and 2. The average rates of the three herbicides, i.e., terbuchlor, triallate and a mixture of the two, required to control 85% of the weeds ($GR_{85}$), and the average maximum rates of the herbicides for 15% or less growth reduction ($GR_{15}$) of the crop plants is shown for illustrative purposes.

A Tammes isobole graphic representation of the synergistic effect of terbuchlor/triallate combinations shows on a coordinate graph the concentration in kg/ha required to achieve $GR_{85}$, for example, with triallate rates shown along the ordinate (horizontal axis) and terbuchlor rates shown along the abscissa (vertical axis). A line is then drawn to join the $GR_{85}$ rates for each compound; this line is the additive isobole for the mixture. Then holding one of the component rates constant while varying the rate of the other component, data points for each $GR_{85}$ rate are fixed on the graph. Any combination of weight ratios of the components falling inside (or under) the additive isobole and having a $GR_{85}$ rate for weeds should exhibit synergism, and the corresponding interpolated curve is termed the synergistic isobole. Combinations whose $GR_{85}$ data points fall outside (or above) the additive isobole should exhibit antagonism and the corresponding interpolated curve is termed the antagonistic isobole. Data points falling on the additive isobole line itself represent mixtures whose combined components have only additive effects. If a particular herbicidal combination has a $GR_{85}$ rate for weeds within the area under the additive isobole for that combination, but the data also exhibits injury to the crop greater than 15% at that rate, obviously, the herbicidal combination may not be selective for use in that particular crop under the specific test conditions.

Figure 2:
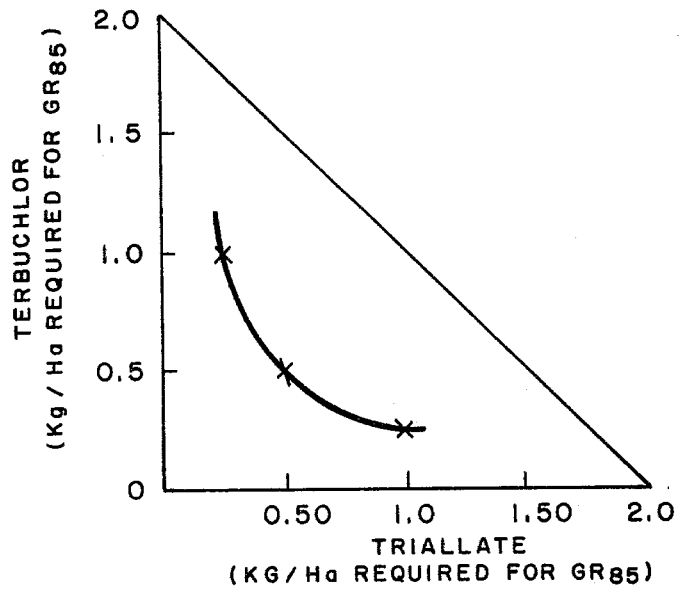

In a specific application of the Tammes isoboles method, data tabulated in FIGS. 1 and 2 show the application rates (in kg/ha) for the individual components terbuchlor and triallate and various concentration ratios of each in mixtures thereof required to achieve $GR_{85}$ for the specific weeds *Galium aparine* and *Chenopodium album*, respectively, in wheat, barley and sugarbeets. Data points for the $GR_{85}$ rates are fixed on the graph below the additive isobole and a line of best fit is drawn through the data points to derive a curve termed the "interpolative synergistic isobole".

The active ingredient herein can be admixed with one or more adjuvants which can be solid or liquid extenders, carriers, diluents, conditioning agents and the like to form herbicidal compositions. Herbicidal compositions containing the active ingredients of this invention can be formulated with or in the form of granules, wettable powders, aqueous suspensions, dust formulations, emulsifiable oils and solutions in solvents. In general, these formulations can all contain one or more surface-active agents.

Surface-active agents which can be used in herbicidal formulations are well known to those skilled in the art and have been well documented in patents, bulletins and textbooks.

The preparation, formulation and particle size of the granules, wettable powders, aqueous suspensions, dusts, emulsifiable oils and solutions in solvents are also well known to those skilled in the art and well documented.

The active ingredient is usually present in the herbicidal compositions in a range of about 0.5 to 95 parts by weight per 100 parts by weight of wettable powder and dust formulations and from about 5 to 95 parts by weight per 100 parts by weight emulsifiable oil formulations. Formulations containing more or less than the above quantities of active ingredient can easily be prepared by those skilled in the art.

The quantity of active ingredient to be used in the field may vary within certain limits depending upon variables known to those in the art, e.g., condition of the soil, climate, plants, etc. In general, however, amounts ranging from about 0.05 to 6.0 or more kg/ha should be adequate; a preferred range being from about 0.125 to 4.0 kg/ha or suitably, an amount within the range of from 0.250 to 2.0 kg/ha. Terbuchlor/triallate ratios may vary within fairly wide limits, e.g., from 1:8 to 8:1, a preferred ratio being within the range of from 1:4 to 4:1 or even 1:2 to 2:1.

Modes of application of the herbicidal compositions of this invention to the plant are well-known to those skilled in the art. The application of liquid and particulate solid herbicidal formulations to the above-ground portions of plants can be carried out by conventional methods, e.g., power dusters, boom and hand sprayers and spray dusters. Although in more practical and recommended usage, the herbicidal compositions herein should be applied simultaneously as conjugate components in a mixture. However, it is within the purview of this invention to apply the individual components sequentially in either order, the time interval between successive applications being such as to accomplish the object of this invention, i.e., the supplementary/complementary/synergistic effects of terbuchlor/triallate combination.

While the illustrative embodiments of the invention have been described herein before with particularity, it will be understood that various other modifications will be apparent to and can readily be made by those skilled in the art without departing from the scope and spirit of the invention. Accordingly, it is not intended that the scope of the claims appended hereto be limited to the examples and description set forth herein but rather the claims be construed as encompassing all the features of patentable novelty which reside in the present invention including all features which would be treated as equivalents thereof by those skilled in the art to which the invention pertains.

I claim:

1. A herbicidal composition consisting essentially of a herbicidally effective amount of a mixture of (a) N-(butoxymethyl)-6'-tert-butyl-2-chloro-o-acetotoluidide and (b) S-(2,3,3-trichloroallyl) N,N-diisopropylthiocarbamate wherein the ratio of (a) to (b) is within the range of from about 1:4 to 4:1.

* * * * *